United States Patent [19]
Herron et al.

[11] Patent Number: 5,932,746
[45] Date of Patent: Aug. 3, 1999

[54] VANADIUM CATALYSTS AND THEIR PRECURSORS

[75] Inventors: Norman Herron, Newark, Del.; David Lincoln Thorn, West Chester, Pa.

[73] Assignee: E. I. du Pont de Nemours and Company, Wilmington, Del.

[21] Appl. No.: 08/847,411

[22] Filed: Apr. 28, 1997

Related U.S. Application Data

[60] Provisional application No. 60/016,398, Apr. 29, 1996.

[51] Int. Cl.[6] .................. C07D 307/34; B01J 27/198; B01J 23/16

[52] U.S. Cl. .................. 549/260; 502/209; 502/210; 502/211; 502/213; 502/214; 502/247; 502/312; 502/353; 502/162; 502/200; 556/24; 556/26; 548/8; 548/113; 548/122; 548/348; 549/259

[58] Field of Search .................. 502/209, 210, 502/211, 213, 214, 247, 312, 353, 162, 200; 556/24, 26; 546/8, 113, 122, 348; 549/260

[56] References Cited

U.S. PATENT DOCUMENTS

| | | | |
|---|---|---|---|
| 3,977,998 | 8/1976 | Freerks et al. | 502/209 |
| 4,165,299 | 8/1979 | Pedersen | 252/435 |
| 4,247,419 | 1/1981 | Vartuli et al. | 252/435 |
| 4,292,201 | 9/1981 | Vartuli et al. | 252/435 |
| 4,333,853 | 6/1982 | Milberger et al. | 252/435 |
| 4,359,405 | 11/1982 | Mount et al. | 502/209 |
| 4,360,453 | 11/1982 | Lemanski et al. | 252/435 |
| 4,396,535 | 8/1983 | Bremer et al. | 502/209 |
| 4,528,280 | 7/1985 | Wrobleski | 502/209 |
| 4,563,439 | 1/1986 | Bremer et al. | 502/209 |
| 4,567,158 | 1/1986 | Wrobleski et al. | 502/209 |
| 4,569,925 | 2/1986 | Yang et al. | 502/209 |
| 4,677,084 | 6/1987 | Bergna | 502/8 |
| 4,699,985 | 10/1987 | Bither, Jr. | 549/260 |
| 5,137,860 | 8/1992 | Ebner et al. | 502/209 |
| 5,326,886 | 7/1994 | Shultz | 549/259 |
| 5,364,824 | 11/1994 | Andrews et al. | 502/209 |
| 5,521,134 | 5/1996 | Bortinger et al. | 502/39 |
| 5,543,532 | 8/1996 | Kourtakis et al. | 549/260 |
| 5,641,722 | 6/1997 | Mitchell et al. | 502/353 |

FOREIGN PATENT DOCUMENTS 0 466 480 A1   1/1992   European Pat. Off. ....... B01J 27/198

OTHER PUBLICATIONS

Chen and Zubieta, Angew. Chem. Int. Ed. Engl., 32, 261–263, Sep. 1992.
Chen and Zubieta, Inorg. Chem., 32, 4485–4486, Apr. 1993.
N. Herron, D. L. Thorn and R. L. Harlow, Molecularly Designed Ultrafine/Nanostructured Materials, Mat. Res. Soc. Symp. Proc., 351, 31–42, 1994, Month N/A.
A. Hasegawa, Electron Spin Resonance of a Trinuclear Vanadyl Pyrophosphate Complex, The Journal of Chemical Physics, 55, 7, 3101–3104, Oct. 1971, Apr. 1970.
C. C. Parker, R. R. Reeder, L. B. Richards and P. H. Rieger, A Novel Vanadyl Pyrophosphate Trimer, Journal of the American Chemical Society, 92:17, 5230–5231, Aug. 1970.
J. Salta, Q. Chen, Y–D. Chang and J. Zubieta, The Oxovanadium–Organophosphonate System: Complex Cluster Structures, etc., Angew. Chem. Int. Ed. Engl., 33:7, 757–759, 1994, Oct. 1993.
F. Cavani and F. Trifiro, Catalyzing Butane Oxidation to Make Maleic Anhydride, ChemTech, 18–24, 1994, Month N/A.

Primary Examiner—Mark L. Bell
Assistant Examiner—Patricia L. Hailey

[57] ABSTRACT

Readily processible cluster compositions of vanadium and phosphorus are precursors to vanadium-phosphorus catalysts including vanadyl pyrophosphate and vanadylbis (metaphosphate).

18 Claims, 3 Drawing Sheets

VANADIUM CATALYSTS AND THEIR PRECURSORS

CROSS REFERENCE TO RELATED APPLICATIONS

This application claims the priority benefit of U.S. Provisional Application No. 60/016,398, filed Apr. 29, 1996.

FIELD OF THE INVENTION

This invention generally relates to readily processible cluster compositions of vanadium and phosphorus which are precursors to vanadium-phosphorus catalysts including vanadyl pyrophosphate and vanadylbis(metaphosphate). The invention also relates to processes for making the cluster compositions, and processes for converting the precursors to vanadium-phosphate catalysts.

BACKGROUND OF THE INVENTION

Vanadyl pyrophosphate $(VO)_2P_2O_7$ (hereinafter generally referred to as "VPO") is the active catalyst used in several commercial processes which convert butane directly to maleic anhydride via air oxidation. The catalyst is believed to perform the selective oxidation of butane via utilization of its lattice oxygen from only the outermost surface layers of the VPO crystallites. Given the accumulated evidence of only surface layer involvement in this oxidation process, there have been numerous efforts to maximize surface area of the catalyst crystallites.

The desire for high surface area has been the basis of a previous synthetic approach to obtaining VPO catalysts (see U.S. Pat. No. 4,360,453). The procedure involves a lengthy alcohol-based preparation starting from vanadium (V) oxide and uses an easily oxidized alcohol such as benzyl alcohol as a reducing agent. The procedure yields a plate-like precursor material $(VO)(HPO_4) \cdot 0.5H_2O$ which may be "calcined and activated" for a long period of time in butane/air mixtures during which time a "topotactic transformation" to VPO occurs. The plate-like, crystalline morphology of the precursor is maintained during this transformation and this morphology is believed to be the reason for the high activity of catalyst prepared in this manner as compared to crystallographically identical material prepared by other (e.g., aqueous) routes.

Another related vanadium and phosphorus containing material is $VO(PO_3)_2$, vanadylbis (metaphosphate). This material can also be used as a catalyst in hydrocarbon, more specifically butane, oxidation processes.

A prime characteristic of a catalytic substance, in addition to its function as a catalyst, is that it possess sufficient mechanical strength to withstand any of the forces it may be subject to during its manufacture and transport and also during its use. The catalyst must be available in a mechanical form sufficiently robust to withstand any forces due to thermal stress and/or agitation it may experience during use. Currently, known VPO catalyst precursor crystallites are spray dried with a silica precursor to form silica/VPO shell composite structures which possess improved attrition resistance when compared to non-silica strengthened VPO (see U.S. Pat. No. 4,677,084). The net result of very specific demands on catalyst physical and chemical performance characteristics is that catalyst costs are significantly increased.

Chen and Zubieta (Angew. Chem. Int. Ed. Engl. 1993, 32, 261–263) describe a phenylphosphonato cluster which has a "reentrant" vanadyl group. The exposed vanadyl site in this compound has a bound methoxy group, but potential Lewis acidity or exchange chemistry is also not discussed. Thermal decomposition is not discussed.

Chen and Zubieta (Inorg. Chem. 1993, 32, 4485–4486) describe dimeric compounds having two vanadyl groups and two bridging phosphonato groups. Here also, Lewis acidity and thermal decomposition are not discussed.

There are several other molecular organophosphorus-vanadium compounds in the open literature. However, none have a V:P ratio of 1:2. Therefore, in order to overcome some of the problems and deficiencies of the prior art, the present invention provides vanadium (IV) cluster compositions which are readily synthesized from simple reagents and which are single-molecule, highly processible precursors to vanadium-phosphorus catalyst materials. Deposition of the soluble precursors onto high surface area supports and spray drying of the soluble precursors with additional materials to produce novel catalyst composites are possible using these materials. Many of the results obtainable using the materials of the present invention are unavailable by other traditional routes to vanadium-phosphorus catalysts.

New methods for preparation of vanadium-phosphorus catalysts can have potential impact in their own right given the sensitivity of the activity and selectivity of vanadium-phosphorus catalysts to preparation protocols. Additionally, the versatility of these cluster species to possible processing alternatives such as spray drying and/or deposition onto high surface area or attrition resistant supports provides a previously unavailable route to new catalyst compositions.

Other objects and advantages of the present invention will become apparent to those skilled in the art upon reference to the attached drawings and to the detailed description of the invention which hereinafter follows.

SUMMARY OF THE INVENTION

The present invention provides a vanadium (IV) cluster of the composition $[A-H^+]_4[(VO)_4(P_2O_7)_2(CH_3O)_4]^{4-}$ where A is a non-coordinating organic base. This cluster can be pyrolyzed to vanadyl pyrophosphate, $(VO)_2P_2O_7$, a useful oxidation catalyst.

The invention further provides a vanadium (IV) cluster of the composition $(VO)_3((RO)_2PO_2)_6 \cdot LB$, where LB is a Lewis base and R is a $C_2-C_{10}$ alkyl containing at least one beta-hydrogen atom. This cluster can be pyrolyzed to vanadylbis (metaphosphate), $VO(PO_3)_2$, a useful oxidation catalyst.

The invention further provides a process for preparing $[A-H^+]_4[(VO)_4(P_2O_7)_2(CH_3O)_4]^{4-}$ comprising reacting $VOSO_4 \cdot H_2O$ with pyrophosphoric acid in the presence of a non-coordinating organic base, A, and isolating the vanadium (IV) cluster, $[A-H^+]_4[(VO)_4(P_2O_7)_2(CH_3O)_4]^{4-}$. Reacting a solution of $[A-H^+]_4[(VO)_4(P_2O_7)_2(CH_3O)_4]^{4-}$ with an excess of a second non-coordinating organic base, A', affords the analogous cluster, $[A'-H^+]_4[(VO)_4(P_2O_7)_2(CH_3O)_4]^{4-}$.

The invention further provides a process for preparing $(VO)_3((RO)_2PO_2)_6 \cdot LB$, comprising reacting $VO(O^iPr)_3$ with dialkyl phosphate, $(RO)_2PO_2H$, and then reacting the resultant oil product with a suitable Lewis base, LB. Reaction with an excess of a second suitable Lewis base, LB', affords the analogous cluster, $(VO)_3((RO)_2PO_2)_6 \cdot LB'$.

The invention also provides supported catalyst precursors derived from the above clusters, $[A-H^+]_4[(VO)_4(P_2O_7)_2(CH_3O)_4]^{4-}$ and $(VO)_3((RO)_2PO_2)_6 \cdot LB$, and the corresponding supported vanadium-phosphorus catalysts obtained by pyrolyzing the supported catalyst precursors.

DETAILED DESCRIPTION OF THE PREFERRED EMBODIMENTS

Figure 1:
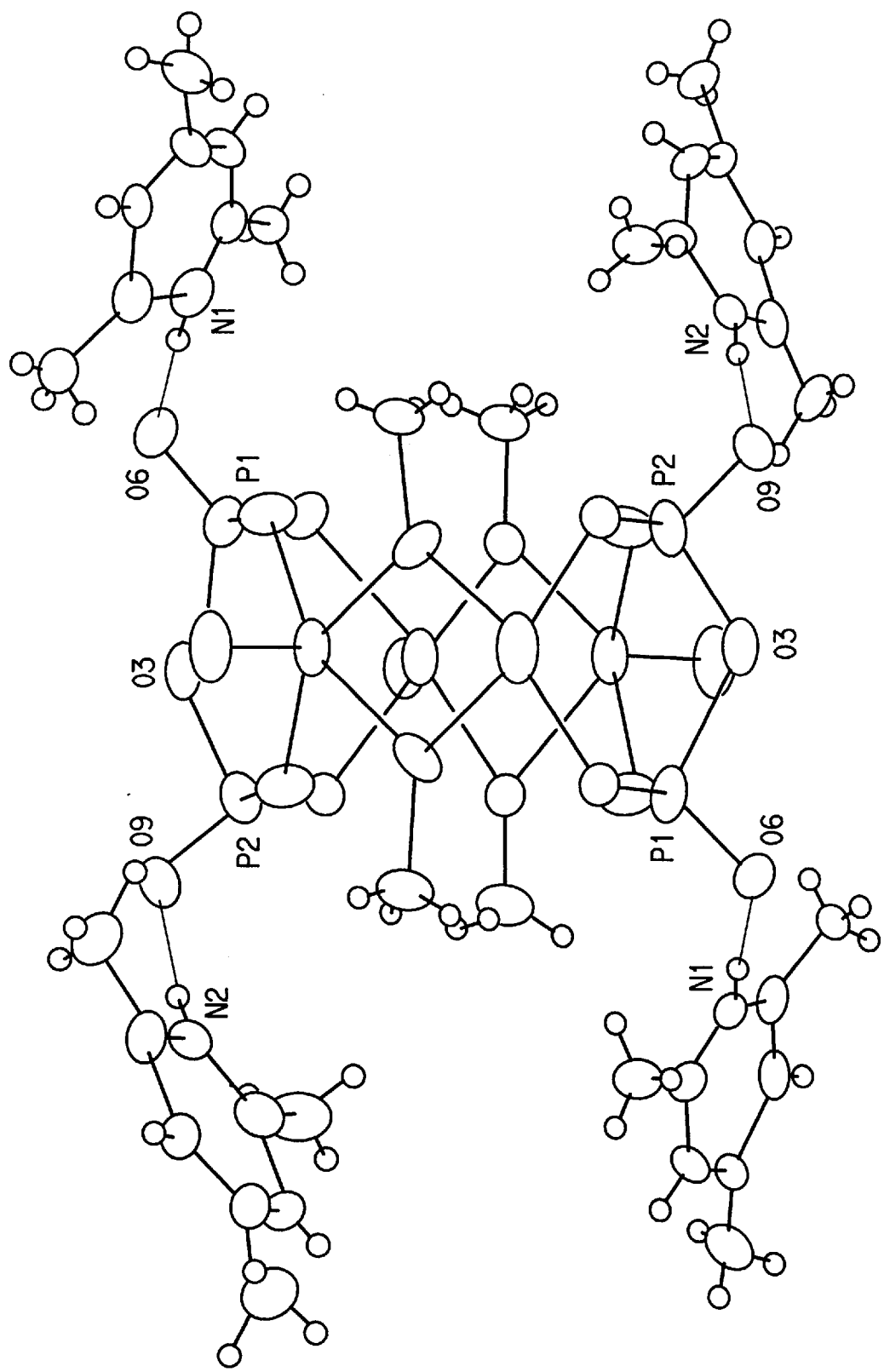
FIG. 1 illustrates the single crystalline structure of $(C_8H_{12}N^+)_4[(VO)_4(P_2O_7)_2(CH_3O)_4]^{4-}$ as revealed by X-ray analysis.

The present invention provides new compositions of matter, easily processible into known vanadium-phosphorus catalyst materials. The solubility and thermal properties of the precursors enable new supported catalyst composites to be readily prepared which may exhibit increased surface area, improved attrition resistance and other tailored properties. The precursors are available from simple, readily available reagents in high yield. Use of the materials of the present invention provides viable alternatives to current multi-step preparations of vanadium-phosphorus catalysts.

The invention also concerns methods to make supported or unsupported vanadyl pyrophosphate (VPO) and vanadyl-bis (metaphosphate) $VO(PO_3)_2$.

One of the novel cluster species of the invention is the catalyst precursor, $[A-H^+]_4[(VO)_4(P_2O_7)_2(OCH_3)_4^{4-}]$, where A is a non-coordinating organic base. Suitable bases, A, include sterically hindered tertiary aliphatic and aromatic amines such as collidine (2,4,6-trimethylpyridine), proton sponge (1,8-bisdimethylaminonaphthalene=PS), and lutidine (2,6-dimethylpyridine). The novel cluster species $[A-H^+]_4[(VO)_4(P_2O_7)_2(OCH_3)_4^{4-}]$ can be prepared using a variety of different non-coordinating bases, resulting in clusters which may be extremely soluble in organic solvents. The vanadium (IV) cluster species can be prepared by a simple reaction between vanadium (IV) sulfate and pyrophosphoric acid in methanol solution in the presence of a non-coordinating organic base and isolating the product, e.g., by crystallization.

When collidine is used as the base, the cluster $(C_8H_{12}N^{30})_4 [(VO)_4(P_2O_7)_2(CH_3O)_4]^{4-}$ crystallizes directly from the synthesis solution in excellent yield (>85%). X-ray analysis of these crystals reveals the structure depicted in FIG. 1. The cluster anion is tetrameric with 4 vanadyl units bridged by pyrophosphato groups and methoxide groups such that each V is in square-pyramidal coordination. The counter cations (collidinium ions) are hydrogen-bonded to the terminal oxygen of the pyrophosphate groups.

These cations may be exchanged either partially or quantitatively for other cations such as protonated 1,8-bisdimethylaminonaphthalene (PSH$^+$), and in this latter case the resultant salt is extremely soluble in methanol solvent. Recrystallization from methanol and x-ray analysis reveals that the tetrameric anion remains intact and that now each terminal oxygen of the pyrophosphate is hydrogen-bonded to a methanol of crystallization. (see FIG. 2)

If the cation, A–H$^+$, is chosen appropriately, the cluster may be thermally decomposed directly to crystalline VPO. The pyrolysis can be carried out from about 350–800° C., preferably from about 500–750° C. VPO is a species of commercial interest as a catalyst for oxidation processes.

Thus, the novel cluster and a process for its conversion to VPO by thermal decomposition are also of commercial import. The cluster provides various processing options which are unavailable via the traditional synthetic routes to VPO.

Thermogravimetric analysis of these salts reveals that they quantitatively lose methanol and the parent base of the organic cation in the 150–500° C. range leaving behind a material of precise stoichiometry $(VO)_2(P_2O_7)$ (i.e., VPO). X-Ray diffraction analysis reveals that at this point the VPO is amorphous but on further annealing at 750° C. the material crystallizes to produce a well-defined VPO diffraction pattern.

Figure 3:
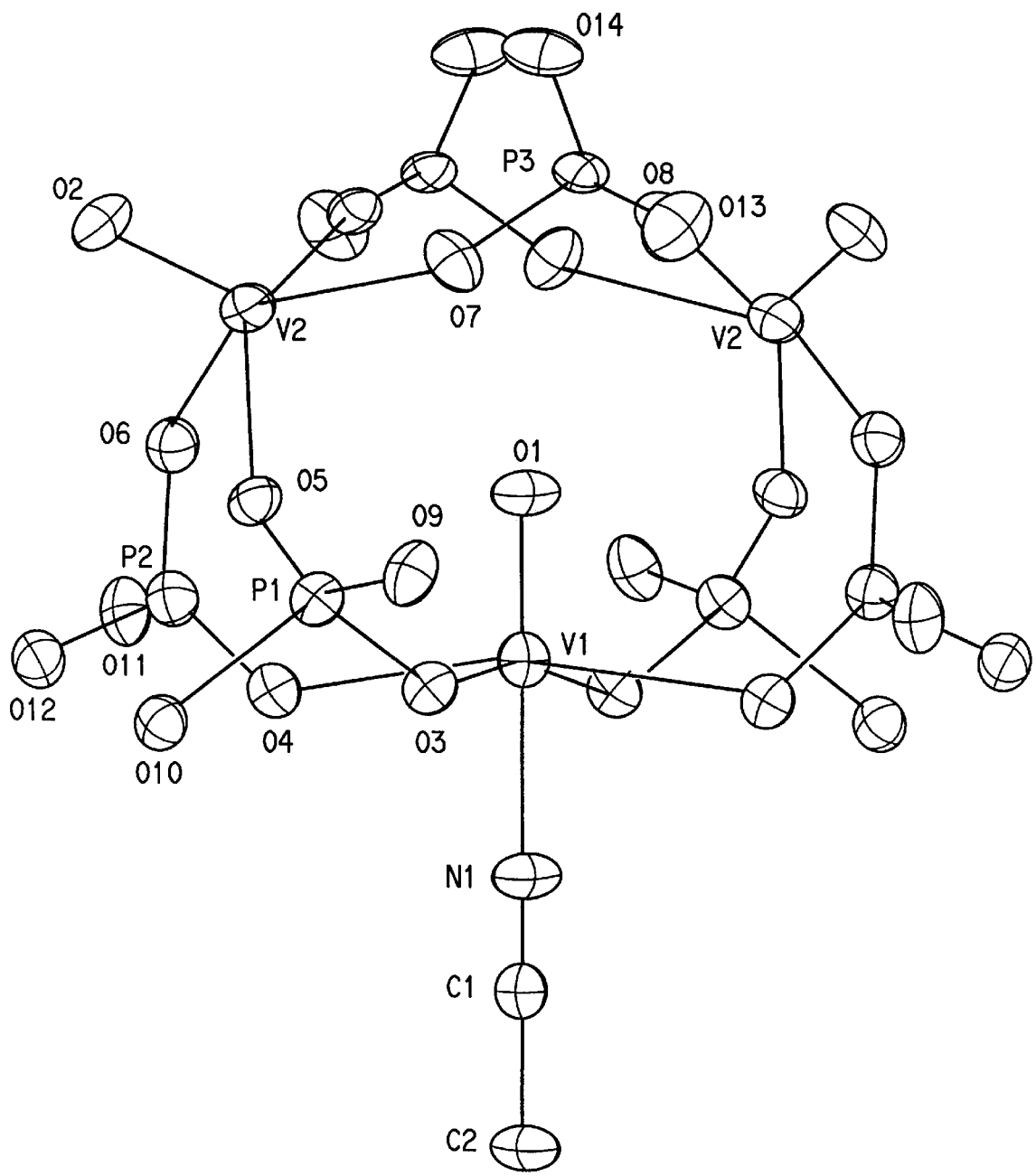
FIG. 3 illustrates the single crystalline structure of $(VO)_3((EtO)_2PO_2)_6 \cdot LB$, where LB is acetonitrile, as revealed by X-ray analysis (hydrogen atoms and ethyl carbon atoms have been omitted for clarity).

Well-defined clusters with V:P=1:2 which can be pyrolyzed to vanadylbis(metaphosphate) are also provided by this invention. These clusters have the composition $(VO)_3((RO)_2PO_2)_6 \cdot LB$, where LB is a Lewis base, such as non-hindered nitriles, aldehydes, ketones, amides, esters, or carboxylic anhydrides, and R is a $C_2-C_{10}$ alkyl containing at least one beta-hydrogen atom (e.g., Et). Preferably, LB is acetonitrile, or tetrahydrofuran (THF). These clusters are prepared most easily by reacting diethylphosphate with a source of vanadium (V), such as $VO(O^iPr)_3$, and a suitable reducing agent, such as the isopropanol formed in the reaction between $VO(O^iPr)_3$ and diethylphosphate, and reacting the resulting product with a Lewis base, LB, and finally isolating the adduct, $(VO)_3((RO)_2PO_2)_6 \cdot LB$. Isolation is best done by adding a non-polar hydrocarbon solvent to the vanadium/phosphate/LB mixture and allowing the $(VO)_3((RO)_2PO_2)_6 \cdot LB$ to crystallize, then isolating the crystalline product. The structure is shown in FIG. 3 wherein R is Et. Other vanadium (V) species which may be used include alkoxyvanadates, such as $VO(OMe)_3$, $VO(OEt)_3$, $VO(O^nPr)_3$ and $VO(O^tBu)_3$, provided a suitable reducing agent is also present. Suitable reducing agents are readily oxidizable primary or secondary alcohols, such as benzyl alcohol or isopropanol. Other phosphates which may be used include dialkylphosphates which contain beta-hydrogen atoms, since these allow facile loss of the organic fragment upon thermolysis.

Reaction of $(VO)_3((RO)_2PO_2)_6 \cdot LB$ with a different suitable Lewis base, LB', will result in partial or complete exchange to give $(VO)_3((RO)_2PO_2)_6 \cdot LB'$.

Thermolysis of $(VO)_3((RO)_2PO_2)_6 \cdot LB$ at about 80° C. results in loss of the Lewis base if it is volatile at this temperature and then loss of water and various organic fragments at temperatures from about 250–600° C. to give material of nominal composition $VO(PO_3)_2$. Preferably, the thermolysis is carried out from about 300–500° C.

The soluble nature of these two types of catalyst precursors allows facile deposition on various support materials. Suitable supports are those having a high surface area to maximize dispersion of the VPO material, and with thermal stability to >500° C. to enable processing. Specific support materials include silica powder, granulated sol-gel derived silica, ceria, zeolite HY, zirconia and titania. Supported catalysts are prepared by adding a support material to a solution of the catalyst precursor in a suitable solvent, optionally stirring the resulting slurry, removing the solvent, and then calcining the supported catalyst precursor to give supported catalyst.

The utility of the clusters is as precursors to catalysts which are, in turn, useful in butane oxidation. The catalysts can be used for butane oxidation according to known processes, including, for example, the process disclosed in allowed U.S. Pat. No. 5,543,532 (Kourtakis et al.), the entire contents of which are incorporated herein.

The invention will now be further described by the following non-limiting examples.

EXAMPLE 1

$(C_8H_{12}N)_4[(VO)_4(P_2O_7)_2(OCH_3)_4]$

Under an inert atmosphere of nitrogen in a glove box, 0.47 g (2 mM) vanadyl sulfate ($VOSO_4 \cdot 4H_2O$) was dissolved into 3 mL collidine (2,4,6-trimethylpyridine) and 7 mL methanol. The resultant solution was warmed to almost boiling, and a second solution of 0.18 g (1 mM) pyrophosphoric acid in 5 mL methanol was added with stirring. The deep blue, clear solution was boiled for 5 minutes and then allowed to cool slowly overnight. Bright blue crystals of the collidinium salt were collected by filtration—yield 0.50 g (85%). Crystals were analyzed by X-ray crystallography; the structure is shown in FIG. 1.

EXAMPLE 2

Figure 2:
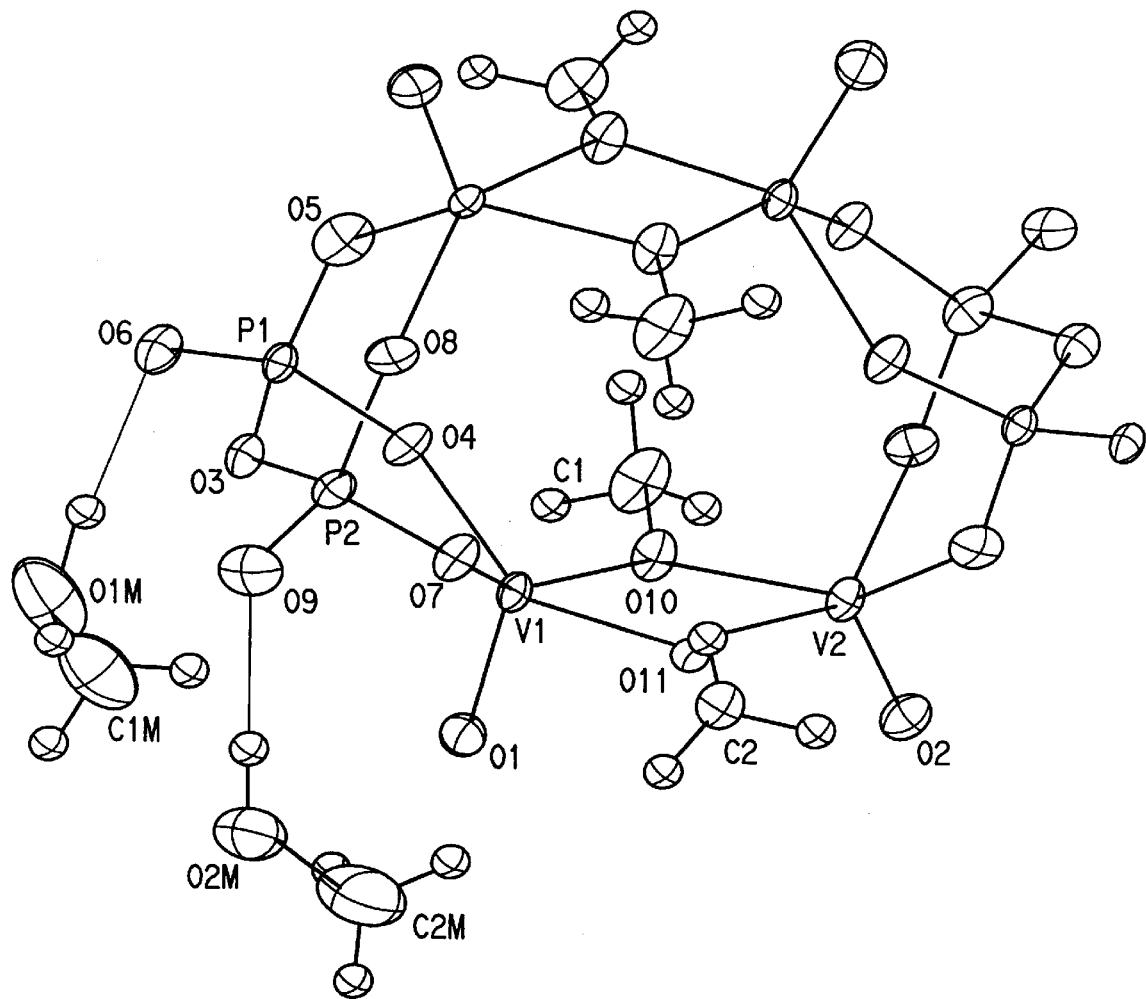
FIG. 2 partially illustrates the single crystalline structure of $(PSH^+)_4[(VO)_4(P_2O_7)_2(CH_3O)_4]^{4-} \cdot 4CH_3OH$ as revealed by X-ray analysis. The $(PSH^+)$ cations and two methanols have been omitted for clarity.

$(C_{14}H_{19}N_2)_4[(VO)_4(P_2O_7)_2(OCH_3)_4] \cdot 4MeOH$ 0.123 g (0.1 mM) of the cluster crystals prepared above was dissolved in a solution of 0.085 g (0.4 mM) 1,8-bis-dimethylaminonaphthalene (proton sponge) in 5 mL methanol. The solution was stirred until completely clear and then allowed to evaporate to dryness. Large blue, diamond-shaped crystals were analyzed by X-ray crystallography. The structure is shown in FIG. 2 and is essentially the same cluster anion but with proton sponge cations rather than collidinium cations and with additional methanol of salvation. Yield in this step is quantitative.

Thermal analysis of both crystalline compounds reveals weight losses from the original materials under flowing nitrogen or air consistent with loss of the cation methoxide equivalent, leaving a material of stoichiometry $(VO)_2P_2O_7$ in the 400–500° C. region. Calcination to >700° C. formed well-crystallized vanadyl pyrophosphate.

EXAMPLE 3

$(VO)_3((EtO)_2PO_2)_6 \cdot CH_3CN$

Diethylphosphate (5.11 g) (purchased from Eastman Chemical, Kingsport, Tenn.) and $VO(O^iPr)_3$ (2.67 g) (purchased from Alfa/Johnson Matthey, Ward Hill, Mass.) were warmed to 60–90° C. in a beaker open to a nitrogen atmosphere. This gave blue to blue-green oils from which crystals were obtained by dissolving the oil in the minimum amount of acetonitrile and layering with hexane. X-ray structure determination revealed the composition of the material to be $(VO)_3((EtO)_2PO_2)_6 \cdot CH_3CN$ and its structure to be a cyclic trimer having two vanadyl V=O groups pointing to the exterior and one vanadyl V=O group pointing to the interior. (see FIG. 3) The inward-pointing vanadyl group (the "reentrant" group) exposes a coordination site to the exterior of the trimer, at which site the acetonitrile is bound. All the vanadium is in the +4 oxidation state, indicating that a redox reaction had occurred, since the starting compound has vanadium only in the +5 oxidation state.

Thermolysis of the complex revealed loss of $CH_3CN$ (at about 80° C.) then loss of ethylene, ethanol, water and diethyl ether, in undetermined ratio, but with average overall composition approximately "$C_4H_{10}O$" (at about 300° C.), resulting in a material of nominal composition $VO(PO_3)_2$.

Other common Lewis bases will replace the acetonitrile, for example, THF, forming a material with the expected composition $(VO)_3((EtO)_2PO_2)_6 \cdot THF$. Replacement of acetonitrile by THF was confirmed by nuclear magnetic resonance (NMR), but the precise composition was not determined.

EXAMPLE 4

$(VO)_3((EtO)_2PO_2)_6 \cdot CH_3CN$ $VO(O^iPr)_3$ (1.86 g, 7.6 mM) and diethylphosphate (2.46 g, 16.0 mM) were combined and warmed to about 70° C., open to the nitrogen atmosphere of a drybox. After about ½ hr the reaction mixture had become a blue paste. This was mixed with about 2 mL acetonitrile and 2 mL isopropanol, boiled gently to make a thick blue solution, then treated with about 100 mL hexane. After standing about 1 hr at room temperature the hexane layer was decanted and fresh hexane was added. After 3 days, blue crystalline solid (1.02 g) was collected.

EXAMPLE 5

$(VO)_3((EtO)_2PO_2)_6 \cdot CH_3CN$ $VO(O^iPr)_3$ (1.58 g, 6.5 mM) and diethylphosphate (2.00 g, 13.0 mM) were combined and treated with 0.35 g benzyl alcohol. The mixture warmed, darkened, and thickened. After standing open to a $N_2$ atmosphere for 3 days, acetonitrile (about 0.5 mL) and hexane (about 10 mL) were added. After an additional day the upper layer (mostly hexane) was decanted and the lower layer treated with acetonitrile (1 drop) and hexane (ca. 10 mL) and left to stand. After an additional day the resulting blue crystalline mass was isolated, washed with hexane and dried briefly in vacuum, and collected (2.05 g).

EXAMPLE 6

Preparation of Silica Powder

Supported VPO Catalyst from Cluster Precursor 1 g of dry silica powder was dried at 200° C. in flowing air for 2 hours. The resultant powder was taken into a nitrogen glove box and slurried into a solution of 1 g of the cluster $(C_{14}H_{19}N_2^+)_4((VO)_4(OCH_3)_4(P_2O_7)_2)^{4-}$ dissolved in 10 mL methanol. The slurry was stirred for 10 mins then evaporated to dryness. The blue solid was collected and placed in a gold foil boat in a horizontal tube furnace. The solid was heated in flowing helium to 820° C. over 1 hour and held there for 4 hours. The resulting dark solid was collected and sent for X-ray diffraction (XRD) analysis. The XRD pattern revealed a strong amorphous background signal from the silica but with peaks for vanadyl pyrophosphate superimposed on this background.

EXAMPLE 7

Preparation of Zirconia and Titania

Supported VPO Catalyst from Cluster Precursor

Example 6 was repeated except that zirconia particles were used in place of the silica powder. This yielded a zirconia supported catalyst.

The procedure was further applied to yield a titania supported catalyst.

EXAMPLE 8

Preparation of Silica Granule

Supported VPO Catalyst from Cluster Precursor 1 g of silica granules (dried at 200° C.) was slurried into a solution of 300 mg $(C_{14}H_{19}N_2^+)_4((VO)_4(OCH_3)_4(P_2O_7)_2)^{4-}$ in 10 mL methanol. The slurry was stirred for 10 mins, then evaporated to dryness. The blue solid was collected and placed in a horizontal tube furnace. The solid was heated in flowing air to 500° C. over 1 hour and held there for 10 mins. The grey solid was cooled and collected and sent for x-ray diffraction analysis.

The above procedure was further applied to cerium oxide and zeolite HY support materials.

EXAMPLE 9

Preparation of Silica Granule Supported

VO(PO$_3$)$_2$, Vanadylbis(Metaphosphate) Catalyst from Cluster Precursor 1 g of silica granules (dried at 200° C.) was slurried into a solution of 1 g (VO)$_3$((EtO)$_2$PO$_2$)$_6$•CH$_3$CN in 10 mL acetonitrile. The slurry was stirred for 10 mins then was evaporated to dryness. The blue solid was collected and placed in a horizontal tube furnace. The solid was heated in flowing helium to 550° C. over 1 hour and held there for 1 hour. The grey solid was cooled and collected and sent for x-ray diffraction analysis.

COMPARATIVE EXAMPLES A AND B AND INVENTIVE EXAMPLES 10–16

Use of Supported Catalysts for the Oxidation of Butane

A number of inventive and comparative examples were used in the oxidation of butane and the results are presented in Table 1 below. The results were obtained for the supported catalysts by loading 0.5 g of the sample material into a tubular reactor where the material was exposed to a flow of 1.5 wt. % butane, 10 wt. % oxygen and 88.5 wt. % nitrogen at 400° C. and at a flow rate of 30 mL/min at one atmosphere of pressure. The effluent from the reactor was then analyzed by mass spectrometry and checked for butane consumption (% butane conversion) and maleic anhydride yield (% yield maleic).

TABLE 1

| Example | Catalyst prep; Support | % Butane Conversion | % Yield Maleic |
|---|---|---|---|
| Comparative A | Blank; none | 0 | 0 |
| Comparative B | Standard VPO; none | 55 | 25 |
| Ex. 10 | Ex. 6; silica | 18 | 9 |
| Ex. 11 | Ex. 7; zirconia | 13 | 0 |
| Ex. 12 | Ex. 8; silica | 7 | 2 |
| Ex. 13 | Ex. 9; silica | 43 | 10 |
| Ex. 14 | Ex. 7; titania | 50 | 3 |
| Ex. 15 | Ex. 8; ceria | 9 | 0 |
| Ex. 16 | Ex. 8; zeolite HY | 52 | 0 |

Although particular embodiments of the present invention have been described in the foregoing description, it will be understood by those skilled in the art that the invention is capable of numerous modifications, substitutions and rearrangements without departing from the spirit or essential attributes of the invention. Reference should be made to the appended claims, rather than to the foregoing specification, as indicating the scope of the invention.

What is claimed is:

1. A catalyst precursor of composition [A–H$^+$]$_4$ [(VO)$_4$(P$_2$O$_7$)$_2$(CH$_3$O)$_4$]$^{-4}$, where A is a non-coordinating, sterically hindered tertiary aliphatic or aromatic amine.

2. The catalyst precursor of claim 1 wherein the amine is selected from the group consisting of collidine (2,4,6-trimethylpyridine), protonated (1,8-bisdimethylaminonaphthalene), and lutidine (2,6-dimethylpyridine).

3. A process for preparing [A–H$^+$]$_4$ [(VO)$_4$(P$_2$O$_7$)$_2$(CH$_3$O)$_4$]$^{-4}$, comprising the steps of:

a) reacting VOSO$_4$•H$_2$O and pyrophosphoric acid in the presence of A, where A is a non-coordinating, sterically hindered tertiary aliphatic or aromatic amine; and b) isolating [A–H$^+$]$_4$ [(VO)$_4$(P$_2$O$_7$)$_2$(CH$_3$O)$_4$]$^{-4}$.

4. A process for preparing [A'–H$^{30}$ ]$_4$ [(VO)$_4$(P$_2$O$_7$)$_2$(CH$_3$O)$_4$]$^{-4}$ comprising reacting [A–H$^+$]$_4$[(VO)$_4$(P$_2$O$_7$)$_2$(CH$_3$O)$_4$]$^{-4}$ with A', where A and A' are different non-coordinating, sterically hindered tertiary aliphatic or aromatic amines.

5. The process of claims 3 or 4 wherein the amine is selected from the group consisting of collidine (2,4,6-trimethylpyridine), protonated (1,8-bisdimethylaminonaphthalene), and lutidine (2,6-dimethylpyridine).

6. A catalyst precursor of composition (VO)$_3$((RO)$_2$PO$_2$)$_6$•LB, where LB is a Lewis base selected from the group consisting of non-hindered nitriles, tetrahydrofuran, non-hindered aldehydes, ketones, and carboxylic anhydrides; and R is a C$_2$–C$_{10}$ alkyl containing at least one beta-hydrogen atom.

7. A process for preparing (VO)$_3$((RO)$_2$PO$_2$)$_6$•LB, comprising the steps of:

a) reacting a dialkyl phosphate, (RO)$_2$PO$_2$H, wherein R is a C$_2$–C$_{10}$ alkyl containing at least one beta-hydrogen atom, with a source of vanadium (V) and a reducing agent to form a resultant product; and b) reacting the resultant product with an LB, where LB is a Lewis base selected from the group consisting of non-hindered nitriles, tetrahydrofuran, non-hindered aldehydes, ketones, and carboxylic anhydrides.

8. A process for preparing (VO)$_3$((RO)$_2$PO$_2$)$_6$•LB according to claim 7, comprising the additional step of contacting the resultant product formed in step (b) with a non-polar hydrocarbon solvent.

9. The process of claim 7 wherein the reducing agent is a primary or secondary alcohol.

10. The process of claim 9 wherein the alcohol is benzyl alcohol or isopropanol.

11. A process for preparing (VO)$_2$P$_2$O$_7$ comprising heating [A–H$^+$]$_4$[(VO)$_4$(P$_2$O$_7$)$_2$(CH$_3$O)$_4$]$^{-4}$, where A is a non-coordinating, sterically hindered tertiary aliphatic or aromatic amine, to 350–800° C.

12. A process for preparing VO(PO$_3$)$_2$ comprising heating (VO)$_3$((RO)$_2$PO$_2$)$_6$•LB to 250–600° C., wherein R is a C$_2$–C$_{10}$ alkyl containing at least one beta-hydrogen atom and LB is a Lewis base selected from the group consisting of non-hindered nitriles, tetrahydrofuran non-hindered aldehydes, ketones, and carboxylic anhydrides.

13. A process for oxidizing butane comprising reacting butane with oxygen in the presence of a catalyst selected from the group consisting of (VO$_2$P$_2$O$_7$ prepared according to claim 13, and VO(PO$_3$)$_2$, prepared according to claim 12.

14. The process of claim 13 wherein the catalyst is supported by a support material selected from the group consisting of silica powder, granulated sol-gel derived silica, ceria, zeolite HY, spent VPO catalyst, zirconia and titania.

15. A process for preparing a supported (VO)$_2$P$_2$O$_7$ catalyst comprising:

a) slurrying a support material selected from the group consisting of silica powder, granulated sol-gel derived silica ceria, zeolite HY, spent VPO catalyst, zirconia and titania and [A–H$^+$]$_4$[(VO)$_4$(P$_2$O$_7$)$_2$(CH$_3$O)$_4$]$^{-4}$, wherein A is a non-coordinating, sterically hindered tertiary aliphatic or aromatic amine, in a suitable solvent to form a supported catalyst precursor;

b) removing the solvent; and c) calcining the supported catalyst precursor to provide a supported (VO)$_2$P$_2$O$_7$ catalyst.

16. A supported catalyst prepared according to claim 15.

17. A process for preparing a supported VO(PO$_3$)$_2$ catalyst comprising:

a) slurrying a support material selected from the group consisting of silica powder, granulated sol-gel derived silica ceria, zeolite HY, spent VPO catalyst, zirconia and titania and (VO)$_3$((RO)$_2$PO$_2$)$_6$·LB, wherein LB is a Lewis base selected from the group consisting of non-hindered nitriles, tetrahydrofuran, non-hindered aldehydes, ketones, and carboxylic anhydrides and R is a C$_2$–C$_{10}$ alkyl containing at least one beta-hydrogen atom, in a suitable solvent to form a supported catalyst precursor;

b) removing the solvent; and c) calcining the supported catalyst precursor to provide a supported VO(PO$_3$)$_2$ catalyst.

18. A supported catalyst prepared according to claim 17.

* * * * *